United States Patent [19]

Correia et al.

[11] Patent Number: 5,356,850
[45] Date of Patent: Oct. 18, 1994

[54] CATALYST FOR THE DEHALOGENATION OF α-HALOGENATED CARBOXYLIC ACIDS

[75] Inventors: Yves Correia, Chateau Arnoux; Dominique Jourdain, Saint Auban; Joseph Nowocien; Alexandre Salerno, both of Chateau Arnoux, all of France

[73] Assignee: Societe Elf Atochem S.A., France

[21] Appl. No.: 961,809

[22] Filed: Oct. 16, 1992

[30] Foreign Application Priority Data

Oct. 18, 1991 [FR] France ................ 91 12915

[51] Int. Cl.$^5$ .................. B01J 21/18; B01J 21/06; B01J 23/40; B01J 23/41
[52] U.S. Cl. .................. 502/185; 502/177; 502/178; 502/180; 502/261; 502/262; 502/327; 502/355
[58] Field of Search .............. 502/177, 178, 185, 261, 502/262, 180, 327, 355

[56] References Cited

U.S. PATENT DOCUMENTS

| | | | |
|---|---|---|---|
| 3,803,054 | 4/1974 | Habig et al. | 252/439 |
| 3,864,281 | 2/1975 | Ohorodnik et al. | 252/447 |
| 4,956,326 | 9/1990 | Yoneda et al. | 502/1.78 |
| 5,191,118 | 3/1993 | Correia et al. | 562/604 |

FOREIGN PATENT DOCUMENTS 2645531  10/1990  France .

OTHER PUBLICATIONS

Greenwood et al., Chemistry of the Elements, 1986, p. 1242.

*Primary Examiner*—Johann Richter
*Assistant Examiner*—Michael B. Hydorn
*Attorney, Agent, or Firm*—Morgan & Finnegan

[57] ABSTRACT

The invention relates to a catalyst comprising a rare metal of Group VIII of the Periodic Table of Elements which has been deposited on an inert support and which has been used to dehalogenate α-halogenated carboxylic acids in the presence of hydrogen, and a rare metal of Group VIII of the Periodic Table of Elements which has been deposited on an inert support and which is such that the granulometry of b) is very much lower than that of a) to form a homogeneous mixture as a result of the action of currents of α-halogenated carboxylic acid and hydrogen.

It is particularly useful for regenerating palladium catalysts used in the purification of crude monochloroacetic acid.

7 Claims, No Drawings

CATALYST FOR THE DEHALOGENATION OF α-HALOGENATED CARBOXYLIC ACIDS

FIELD OF THE INVENTION

The present invention relates to a catalyst for the dehalogenation of α-halogenated carboxylic acids. The invention relates particularly to a catalyst to eliminate dichloroacetic acid (DCAA) contained in monochloroacetic acid (MCAA).

BACKGROUND OF THE INVENTION

The synthesis of monochloroacetic acid on an industrial scale is conducted by chlorination of acetic acid, but inevitably dichloroacetic acid, and sometimes a small amount of trichloroacetic acid are formed as well. One thus obtains a crude monochloroacetic acid which is a mixture consisting of monochloroacetic acid, dichloroacetic acid, traces of trichloroacetic acid and unreacted acetic acid. Because of the proximity of the boiling point of MCAA (189° C.) and DCAA (194° C.), it is practically impossible to separate them by distillation. In contrast, it is very simple to hydrogenate this mixture to convert the DCAA into MCAA according to the reaction:

$$CHCl_2COOH + H_2 \rightarrow CH_2ClCOOH + HCl$$

This hydrogenation is not entirely selective and the retrogradation of MCAA into acetic acid is also observed:

$$CH_2ClCOOH + H_2 \rightarrow CH_3COOH + HCl$$

This reaction is conducted with a catalyst and a secondary product of acetaldehyde, which has the drawback of generating condensation products.

The hydrogenation of crude monochloroacetic acid also produces heavy compounds such as glycolic acid monochloroacetate (GAMA).

The hydrogenation of crude monochloroacetic acid occurs in the presence of palladium that is deposited on carbon (coal), alumina, or silica. This method is described, for example, in U.S. Pat. No. 2,863,917 and British Patent No. 1,188,745. French Patent No. 2,647,032 also describes the doping of these palladium catalysts with sulfur or sulfurous compounds. French Patent No. 2,046,424 describes a method for the regeneration of these palladium catalysts. Indeed, these catalysts lose their activity while being used, as well as the selectivity, and they generate more aldehydes than heavy products. According to French Patent No. 2,046,424, one oxidizes used catalysts with gaseous chlorine at a temperature between 100° and 150° C. to convert the palladium into its chloride; then, one reduces this with hydrogen or other reducing agents to again produce the metallic palladium.

SUMMARY OF THE INVENTION

The applicant has found a very simple method to regenerate these catalysts; it is a method to prepare a catalyst which has the properties of a new catalyst from a used catalyst.

The present invention is therefore a mixture of:
a) a rare metal of Group VIII of the Periodic Table of Elements which is deposited on an inert support and which has been used to dehalogenate α-halogenated carboxylic acids in the presence of hydrogen, and
b) a rare metal of Group VIII which has been deposited on an inert support and which is such that the granulometry of b) is much lower than that of a) to form a homogeneous mixture as a result of the effect of currents of α-halogenated carboxylic acids and hydrogen.

Briefly summarized, the invention consists of adding a used catalyst for the dehalogenation of α-halogenated carboxylic acid to fines of new catalyst; the fines mix with the used catalyst as a result of the effect of the carboxylic acid current and the hydrogen current, which thus forms a new catalyst which has the properties of a new catalyst. Another advantage is that the step of stopping production is eliminated, as are the steps of draining the reactor and replacing the catalyst charge.

DETAILED DESCRIPTION OF THE INVENTION

The product described at a) is a catalyst. The rare metals of Group VIII of the Periodic Table of Elements are ruthenium, rhodium, palladium, osmium, iridium and platinum. This metal is deposited on a support such as carbon, silica, silicon carbide, aluminum or boron carbide. The quantity of the rare metal can be between 0.1 and 10% of the entire assembly of rare metal plus support.

The rare metal is advantageously deposited on carbon with a large surface area in an amount of from 0.1 to 5 wt. % of the catalyst, i.e., of the carbon plus metal, and it is spread on the surface of the carbon. A carbon with a large surface is defined here as carbon of approximately 600 m²/g up to 1300 m²/g. This carbon is in the form of small extruded cylinders or in the form of a powder. Preferably, the rare metal is palladium.

As examples of α-halogenated carboxylic acids one can cite the acids with the formula:

$$R_1-\underset{\underset{X}{|}}{\overset{\overset{R_2}{|}}{C}}-COOH \quad (I)$$

in which X is chlorine, $R_1$ and $R_2$ are identical or different and represent X, H, a straight or branched alkyl radical with 1 to 12 carbon atoms or a cycloalkyl radical with 3 to 12 carbon atoms. The invention also applies to esters of the acids width formula (I). These are preferably aliphatic esters with 1 to 10 carbon atoms, and preferably 1 to 5 carbon atoms.

The product of a) is a catalyst which has been used to dehalogenate α-halogenated carboxylic acids, i.e., it gradually has lost a part of its capacity during use. This wear usually is reflected in a decrease of activity; consequently, the temperature has to be increased to reach the same production level with the unchanged weight of catalyst. One also observes an increase in secondary products. One also observes a loss of rare metal. At a) the invention concerns catalysts which have already been used and which must be changed either because they are no longer sufficiently active or because they result in an excess production of secondary products.

Product b) is a product like a) and with a granulometry which is less than that of a) so that it can be mixed readily with a) as a result of the action of currents of α-halogenated carboxylic acids and hydrogen; thus, it can form a homogeneous mixture. It is preferred that b) is active. It can be, for example, fines of new catalyst or new catalyst with small granulometry.

The applicant has discovered that a mixture of a) and b), in spite of the fact that it contains less rare metal than a) in the new state, had the same properties as a) in the new state.

The quantity of b) to be added to a) depends on the desired performance levels. For example, if one wishes to obtain a catalyst which has the same properties and the same production level as a) in the new state, and if a) has been used to such an extent that it has lost 40% of the initial rare metal content, it suffices to add a quantity of b) which ranges from 3 to 10% of the initial weight of a) and which has the same initial content of rare metal. This quantity of b) can vary since one can use a catalyst b) which may be either richer or less rich in rare metal content than a) in the new state. If one wishes to obtain a more-active or less-active catalyst compared to a) in the new state, it suffices to add either more or less b) or catalyst b) which is either more or less rich in rare metal content. The scope of the invention would not be exceeded if a) and b) contained different rare metals or different mixtures of rare metals. The scope of the invention would not be exceeded if a) were a catalyst which has not been used extensively, or by any combination of these possibilities. The scope of the invention would not be exceeded if the mixture a) and b) of the invention contained more rare metal than a) in the new state.

Indeed, if a) in the new state weighs 10,000 g and contains 1% of rare metal, i.e., 100 g, the loss being, for example, 40%, 60 g of metal will remain; thus, one adds 5000 g of b) at 1%, or 50 g, of rare metal. The mixture a)+b) thus contains 110 g of rare metal. One can thus see that by adding 5000 g of new catalyst to 10,000 initial grams of catalyst which has been applied and used up, one obtains a new charge of catalyst using a quantity of catalyst equal to half of the initial charge instead of changing the entire charge.

The invention is particularly useful for the purification of impure mono-α-halogenated carboxylic acids, $R_1CHXCOOH$, with $R_1$ having the above-indicated meaning. These acids are prepared by halogenation of the corresponding acid, $R_1CH_2COOH$, and one gets a mixture of $R_1CHXCOOH$, $R_1CX_2COOH$, unreacted $R_1CH_2COOH$ acid and sometimes traces of $CX_3COOH$ in the particular case of $CH_3COOH$ acid.

One could first separate the $R_1CH_2COOH$ from this mixture, but it is more simple to hydrogenate first:

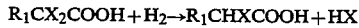

and to then separate, since inevitably a part of the $R_1CHXCOOH$ is converted in the retrogradation into acid according to:

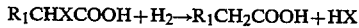

It then suffices to distill the mixture of $R_1CHXCOOH$, $R_1CH_2COOH$ and HX to produce relatively pure $R_1CHXCOO$.

The invention is applicable particularly to the purification of monochloroacetic acid.

The retrogradation ratio equals the ratio between the number of X ions in the purified acid, i.e., those originating from HX, to the theoretical number of X to be removed from $R_1CX_2COOH$, (and possibly $CX_3COOH$) to convert it into $R_1CHXCOOH$. With the exception of $CX_3COOH$, the minimum retrogradation ratio is one. Usually this backward reaction is between 1.4 and 3.4.

This high retrogradation shows that the reaction is not selective and aldehydes and heavy products are produced.

The applicant has observed that by adding fines of new catalyst to the used charge, i.e., by forming a new catalytic charge which consists of the mixture a) and b) according to the invention, one obtains the properties of a charge of new catalyst.

The present invention also relates to a method for the purification of mono-α-halogenated carboxylic acids with formula $R_1CHXCOOH$, with $R_1$ having the above-indicated meaning, characterized in that one uses a catalytic charge which contains a) and b) according to the invention.

EXAMPLE 1

1. Glass column A, with a double envelope with an internal diameter of 26 mm, is loaded with 130 g of an extruded carbon with a diameter of 2 mm and a length of 4 mm, having a specific surface area larger than 700 $m^2/g$ and containing 0.8% palladium deposited on the surface (more than 100 $m^2/g$ of palladium).

This column is then supplied in a concurrent flow with a solution of crude acid (by wt. %): approximately 80% monochloroacetic acid, approximately 4% dichloroacetic acid, approximately 16% acetic acid and a flow of hydrogen with 4 NL [normal liters]/h.

The column is heated to 125° C. and, after approximately 100 h of operation, the following results were obtained as reported in the table under the heading "new catalyst."

2. After several thousand hours of operation, the catalyst becomes used up, see the table, under the heading "used catalyst", and it is thus a catalyst such as a).

The new catalyst contains 0.8% of palladium, or 1040 mg. The used catalyst weights 170 g and contains 0.39% of palladium, or 660 mg.

In the table, "DCAA" designates dichloroacetic acid, "GAMA" designates glycolic acid monochloroacetate, "—CHO" designates aldehydes (expressed in acetaldehyde) in mg/kg of crude acid to be purified.

Cl/DCAA represents the retrogradation. The space velocity of the liquid is the velocity of the crude acid per hour and $m^3$ of catalytic beds.

3. One then adds 13 g of fines of new catalyst in the form of a powder with a particle size of 70 μm consisting of carbon containing 1% palladium, i.e., product b).

One observes that 3.2 g leave the catalytic bed again and 9.8 g remain in the catalyst bed. This addition is conducted without stopping the reaction.

The counting of the hours of the operation is again set to zero and after 282 h one measures the results, see the table under the heading "used catalyst reactivated by the addition of catalyst in powder form."

The performances were measured up to 1200 h and therefore a quantity of 98 mg were added to the catalytic bed. The mixture according to the invention contains 660 mg+98 mg=758 mg of catalyst.

One then notes that one can decrease the temperature of the bed to reach performance levels with regard to the conversion of dichloroacetic acid which are identical to those observed earlier; the contents of the secondary product acetaldehyde and glycolic acid monochloroacetate (GAMA) are decreased considerably in comparison to those observed with the nonreactivated used catalyst; this activity is maintained over time.

result of the action of currents of α-halogenated carboxylic acids and hydrogen.

TABLE

|  | Hours of Operation | Temp °C. | Space Velocity of liquid kg/h/m³ | DCAA % Input/ | Output | GAMA % | CHO mg/kg | Cl-/ DCAA |
|---|---|---|---|---|---|---|---|---|
| Used Catalyst |  | 155 | 249 | 3.35 | 0.17 | 1.45 | 825 | 2.67 |
|  |  | 160 | 261 | 3.35 | 0.14 | 1.40 | 985 | 3.13 |
| Used Catalyst | 282 | 140 | 250 | 3.22 | 0.14 | 0.40 | 402.5 | 1.71 |
| Reactivated by | 434 | 140 | 234 | 2.56 | 0.10 | 0.60 | 340 | 2.10 |
| Addition of Catalyst | 651 | 140 | 255 | 2.97 | 0.16 | 0.70 | 243 | 1.78 |
| In powder form | 742 | 140 | 242 | 2.95 | 0.14 | 0.80 | 254 | 1.89 |
|  | 1200 | 140 | 238 | 3.02 | 0.15 | 0.70 | 290 | 1.84 |
| New Catalysts | 200 | 135 | 241 | 3.29 | 0.17 | 0.33 | 354 | 2.96 |
|  | 250 | 135 | 272 | 3.09 | 0.13 | 0.40 | 308 | 2.98 |

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims. The above references are hereby incorporated by reference.

What is claimed is:

1. Catalyst comprising:
   a) a rare metal of ruthenium, rhodium, palladium, osmium, iridium or platinum which has been deposited on an inert support wherein the inert support is selected from carbon, silica, silicon carbide, aluminum and boron carbide, and which has been used to dehalogenate α-halogenated carboxylic acids in the presence of hydrogen, and
   b) a rare metal of ruthenium, rhodium, palladium, osmium, iridium or platinum which has been deposited on an inert support, wherein the inert support is selected from carbon, silica, silicon carbide, aluminum and boron carbide; and which is such that the granulometry of b) is very much less than that of a), to form a homogeneous mixture as a 2. Catalyst according to claim 1, wherein the rare metal of a) and b) is palladium.

3. Catalyst according to claim 1, wherein the α-halogenated acids have the formula:

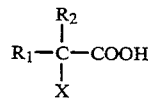

in which X is chlorine; $R_1$ and $R_2$ are identical or different and are X, H, or a straight or branched alkyl radical with 3 to 12 carbon atoms.

4. Catalyst according to claim 1, wherein the inert support is carbon.

5. Catalyst according to claim 4, wherein the surface area of the inert support is between about 600 square meters per gram and 1300 square meters per gram.

6. Catalyst according to claim 1, wherein the quantity of rare metal is between 0.1 and 10 weight % of rare metal plus inert support.

7. Catalyst according to claim 6, wherein the quantity of rare metal is between 0.1 and 5 weight % of rare metal plus support.

* * * * *